(12) United States Patent
Helmer et al.

(10) Patent No.: US 12,109,400 B2
(45) Date of Patent: Oct. 8, 2024

(54) MEDICAMENT ADMINISTRATION DEVICE AND DATA COLLECTION DEVICE

(71) Applicant: SANOFI, Paris (FR)

(72) Inventors: Michael Helmer, Frankfurt am Main (DE); Christian Rehbein, Budenheimer (DE)

(73) Assignee: SANOFI, Paris (FR)

( * ) Notice: Subject to any disclaimer, the term of this patent is extended or adjusted under 35 U.S.C. 154(b) by 469 days.

(21) Appl. No.: 16/757,151

(22) PCT Filed: Oct. 19, 2018

(86) PCT No.: PCT/EP2018/078681
§ 371 (c)(1),
(2) Date: Apr. 17, 2020

(87) PCT Pub. No.: WO2019/077094
PCT Pub. Date: Apr. 25, 2019

(65) Prior Publication Data
US 2020/0276393 A1    Sep. 3, 2020

(30) Foreign Application Priority Data
Oct. 19, 2017  (EP) .................................... 17306413

(51) Int. Cl.
*A61M 5/315*    (2006.01)
*A61M 5/20*     (2006.01)
*A61M 5/31*     (2006.01)

(52) U.S. Cl.
CPC ............ *A61M 5/3155* (2013.01); *A61M 5/20* (2013.01); *A61M 5/31568* (2013.01); *A61M 2005/3126* (2013.01); *A61M 2205/3306* (2013.01); *A61M 2205/52* (2013.01)

(58) Field of Classification Search
CPC .. A61M 5/3155; A61M 5/20; A61M 5/31568; A61M 2005/3126; A61M 2205/3306; A61M 2205/52
See application file for complete search history.

(56) References Cited

U.S. PATENT DOCUMENTS

| | | | |
|---|---|---|---|
| 7,922,699 B2 | 4/2011 | Baba et al. | |
| 9,440,028 B2 | 9/2016 | Baker et al. | |
| 2004/0158205 A1 | 8/2004 | Savage | |
| 2013/0221097 A1 | 8/2013 | Day et al. | |

(Continued)

FOREIGN PATENT DOCUMENTS

| | | |
|---|---|---|
| CN | 103228305 A | 7/2013 |
| CN | 103648552 A | 3/2014 |

(Continued)

OTHER PUBLICATIONS

PCT International Preliminary Report on Patentability in Application No. PCT/EP2018/078681, dated Apr. 21, 2020, 8 pages.

(Continued)

*Primary Examiner* — Lauren P Farrar
(74) *Attorney, Agent, or Firm* — Bond, Schoeneck & King, PLLC

(57) ABSTRACT

The application relates to a data collection device for mounting on a rotatable dose setting dial of a medicament administration device. A system comprising the data collection device and the medicament administration device is also provided.

16 Claims, 5 Drawing Sheets

(56) References Cited

U.S. PATENT DOCUMENTS

| | | |
|---|---|---|
| 2015/0290392 A1 | 10/2015 | Henderson et al. |
| 2016/0193420 A1 | 7/2016 | Marsh |
| 2016/0213855 A1 | 7/2016 | Marsh |
| 2016/0339181 A1* | 11/2016 | Keitel ............... A61M 5/24 |
| 2017/0014577 A1 | 1/2017 | Riedel |
| 2017/0304546 A1* | 10/2017 | Blei ................. A61M 5/31 |
| 2018/0154086 A1* | 6/2018 | Toporek ........... A61M 5/31551 |

FOREIGN PATENT DOCUMENTS

| | | |
|---|---|---|
| CN | 104220116 | 12/2014 |
| CN | 104703641 A | 6/2015 |
| CN | 105682710 A | 6/2016 |
| CN | 105705179 A | 6/2016 |
| CN | 106574897 A | 4/2017 |
| CN | 107106784 | 8/2017 |
| EP | 2514450 A1 | 10/2012 |
| EP | 3045186 A1 | 7/2016 |
| EP | 3058970 | 8/2016 |
| EP | 3103492 | 12/2016 |
| JP | 2018-505007 | 2/2018 |
| JP | 2018-517502 | 7/2018 |
| WO | WO 2003/057286 | 7/2003 |
| WO | WO 2012/072559 A1 | 6/2012 |
| WO | WO 2013/120777 | 8/2013 |
| WO | WO 2013/120778 | 8/2013 |
| WO | WO 2014/173772 A1 | 10/2014 |
| WO | WO 2016/110592 | 7/2016 |
| WO | WO 2016/131713 | 8/2016 |
| WO | WO 2016/169845 | 10/2016 |
| WO | WO 2016/198516 | 12/2016 |
| WO | WO 2017/071983 | 5/2017 |

OTHER PUBLICATIONS

PCT International Search Report and Written Opinion in Application No. PCT/EP2018/078681, dated Jan. 17, 2019, 12 pages.

* cited by examiner

MEDICAMENT ADMINISTRATION DEVICE AND DATA COLLECTION DEVICE

CROSS REFERENCE TO RELATED APPLICATIONS

The present application is the national stage entry of International Patent Application No. PCT/EP2018/078681, filed on Oct. 19, 2018, and claims priority to Application No. EP 17306413.0, filed on Oct. 19, 2017, the disclosures of which are incorporated herein by reference.

TECHNICAL FIELD

The present disclosure relates to a data collection device for attachment to a medicament administration device, a modified medicament administration device and a system comprising both the data collection device and modified medicament administration device.

BACKGROUND

A variety of diseases exists that require regular treatment by injection of a medicament. Such injection can be performed by using medicament delivery devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as a medicament delivery device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing the dosage knob or an injection button of the insulin pen. To be able to monitor insulin injection, for instance to prevent false handling of the insulin pen or to keep track of the doses already applied, it is desirable to measure information related to a condition and/or use of the medicament delivery device, such as for instance information on the injected insulin dose.

SUMMARY

According to a first aspect of the invention there is provided a data collection device for mounting on a rotatable dose setting dial of a medicament administration device, the data collection device comprising:
 a light source; and
 an optical sensor, wherein when the data collection device is mounted on the dose setting dial, the light source is configured to illuminate a portion of a surface of at least one outward radial protrusion extending beyond the external surface of an external housing of the medicament administration device, wherein the at least one outward radial protrusion is part of a dial sleeve located partially inside the outer housing and configured to rotate when a dose is dialed and wherein the optical sensor is configured to receive light reflected by at least relatively reflective regions disposed on the surface of the at least one outward radial protrusion.

In some embodiments, the data collection device has a distal end and a proximal end, wherein the proximal end is closed and the distal end is open to allow the data collection device to be mounted on the rotatable dose setting dial and wherein the light source is configured to project light from the distal end of the data collection device.

In some embodiments, when mounted on the dose setting dial, the distal end of the data collection device faces the at least one outward radial protrusion of the dial sleeve.

In some embodiments, the data collection device comprises an electronics assembly including the light source and the optical sensor.

In some embodiments, the electronics assembly comprises a processor arrangement configured to receive signals from the optical sensor and to detect the occurrence of a medicament delivery from the medicament administration device.

In some embodiments, the processor arrangement is configured to receive signals from the optical sensor and to determine an amount of rotation of the dial sleeve of the medicament administration device.

In some embodiments, the light source is an infrared light source.

In some embodiments, the data collection device is configured to determine a dialed dose.

According to a second aspect of the invention there is provided a medicament administration device comprising:
 a housing having a proximal end and a distal end;
 a rotatable dial sleeve located partially inside the housing, the rotatable dial sleeve having a proximal end and a distal end; and
 a dose setting dial coupled via a clutch to the proximal end of the dial sleeve, wherein the dial sleeve comprises at least one outward radial protrusion arranged between the proximal end of the housing and the dose setting dial.

In some embodiments, the at least one outward radial protrusion extends beyond an external surface of the housing.

In some embodiments, the at least one outward radial protrusion comprises a relatively reflective portion formed on the surface of the at least one outward radial protrusion.

In some embodiments, the at least one outward radial protrusion comprises a plurality of teeth.

In some embodiments, the teeth comprise relatively reflective portions formed on the surface of the teeth.

In some embodiments, the at least one outward radial protrusion is an annular flange.

In some embodiments, the dial sleeve and dose setting dial are rotationally coupled during dose setting of the medicament administration device and rotationally decoupled during dose dispensing of the medicament administration device.

According to a third aspect of the invention there is provided a system comprising:
 a medicament administration device comprising a housing having a proximal end and a distal end;
 a rotatable dial sleeve located partially inside the housing, the rotatable dial sleeve having a proximal end and a distal end;
 a dose setting dial coupled via a clutch to the proximal end of the dial sleeve, wherein the dial sleeve comprises at least one outward radial protrusion arranged between the proximal end of the housing and the dose setting dial and extending beyond an external surface of an external housing of the medicament administration device;

a data collection device configured to be mounted on the rotatable dose setting dial of the medicament administration device, the data collection device comprising:
a light source; and
an optical sensor, wherein the light source is configured to illuminate a portion of a surface of the at least one outward radial protrusion, and wherein the optical sensor is configured to receive light reflected by at least relatively reflective regions disposed on the surface of the at least one outward radial protrusion.

In some embodiments, the data collection device is mounted on the dose setting dial of the medicament administration device.

According to a fourth aspect of the invention there is provided a system comprising the data collection device according to the first aspect of the invention and the medicament administration device according to a second aspect of the invention.

DETAILED DESCRIPTION

Figure 1:
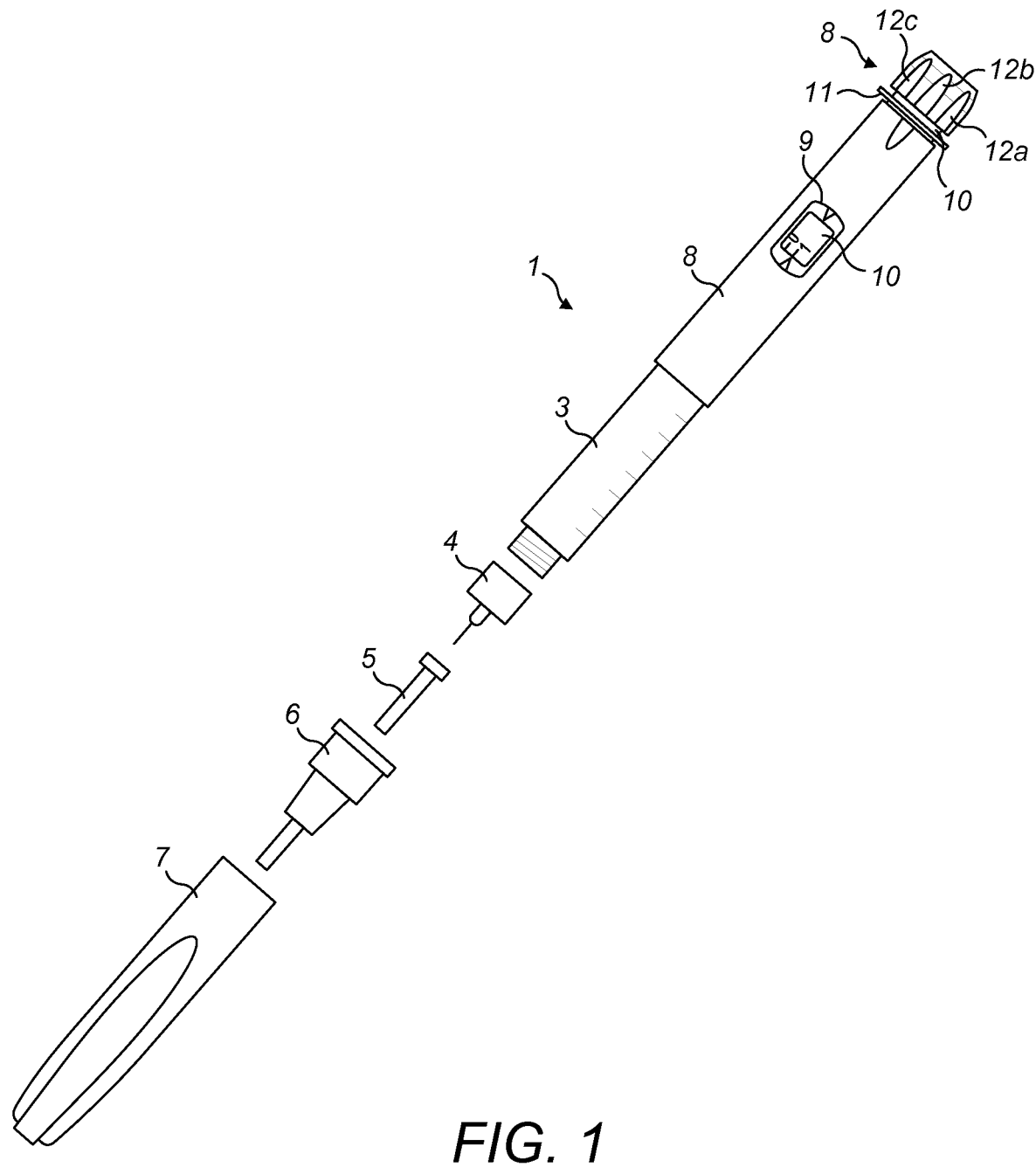
FIG. 1 shows an exploded view of an injection device for use with a data collection device.

FIG. 1 is an exploded view of a medicament administration device. In this example, the medicament administration device is a medicament delivery device 1, such as Sanofi's AllStar® insulin injection pen. However, the present invention is also compatible with other types and makes of injection pens as described below.

The medicament delivery device 1 of FIG. 1 is a pre-filled injection pen that comprises a housing 2 and contains an insulin container 3, to which a needle 4 can be affixed. The medicament delivery device 1 may be disposable or re-usable. The needle 4 is protected by an inner needle cap 5 and either an outer needle cap 6 or an alternative cap 7. An insulin dose to be ejected from medicament delivery device 1 can be programmed, or 'dialed in' by turning a dosage setting dial 8 (also referred to herein as a dose selection element or dosage knob 8), and a currently programmed dose is then displayed via dosage window 9, for instance in multiples of units. For example, where the medicament delivery device 1 is configured to administer human insulin, the dosage may be displayed in so-called International Units (IU), wherein one IU is the biological equivalent of about 45.5 micrograms of pure crystalline insulin (1/22 mg). Other units may be employed in medicament delivery devices for delivering analogue insulin or other medicaments. It should be noted that the selected dose may equally well be displayed differently than as shown in the dosage window 9 in FIG. 1.

The medicament delivery device 1 has distal and proximal ends. The term "distal" refers to a location that is relatively close to the site of injection, and the term "proximal" refers to a location that is relatively further away from the injection site. In the present embodiment, the needle 4 is situated towards the distal end of the device 1, whilst the dose setting dial 8 is situated towards the proximal end of the device 1. The device 1 has a longitudinal axis which extends between the proximal and distal ends of the device 1.

The dosage window 9 may be in the form of an aperture in the housing 2, which permits a user to view a limited portion of a dial sleeve 10 that is configured to move when the dosage knob 8 is turned, to provide a visual indication of a currently programmed dose. For example, the dial sleeve 10 can be a component which rotates when a dose is being dispensed from the medicament delivery device 1. The dial sleeve 10 may comprise a series of indicators, such as numbers and/or other marks, which provide an indication to the user of the currently programmed dose.

The dial sleeve 10 is partially located within the housing 2 and comprises at least one protrusion 11 which extends from the external surface of the dial sleeve 10 beyond the external surface of the housing 2. The protrusion(s) 11 can be positioned between the dosage dial 8 and the proximal end of the housing 2. The protrusion(s) 11 comprises an upper and a lower surface. The upper surface of the protrusion(s) 11 faces the proximal end of the medicament delivery device 1, whilst the lower surface of the protrusion(s) 11 faces the distal end of the medicament delivery device 1. In the example illustrated in FIG. 1, the medicament delivery device 1 is in its pre-dialed state, i.e. a dosage has not yet been dialed. In this state, there is a gap between the lower face of the protrusion(s) 11 and the proximal edge of the housing 2, and a gap between the upper surface of the protrusion(s) 11 and the distal edge of the dose setting dial 8.

In other embodiments, the lower surface of the protrusion(s) 11 may abut the proximal edge of the housing 2.

In this example, the dosage knob 8 includes one or more formations 12a, 12b, 12c that facilitate programming because they improve the grip a user feels when grasping the dosage knob 8. In another example (not shown) the dosage knob does not include formations.

The medicament delivery device 1 may be configured so that turning the dosage knob 8 causes a mechanical click sound to provide acoustical feedback to a user. The dial sleeve 10 mechanically interacts with a piston in insulin container 3. When needle 4 is stuck into a skin portion of a patient, a user depresses the entire dosage knob 8, which moves longitudinally relative to the housing 2 in order to cause the medicament to be dispensed. The insulin dose displayed in display window 9 will be ejected from medicament delivery device 1. When the needle 4 of medicament delivery device 1 remains for a certain time in the skin portion after the dosage knob 8 is pushed towards the distal end of the medicament delivery device, a high percentage of the dose is actually injected into the patient's body. Ejection of the insulin dose may also cause a mechanical click sound, which is however different from the sounds produced when turning dosage knob 8.

During delivery of the insulin dose, the dosage knob 8 is turned to its initial position in an axial movement, that is to say without rotation, while the dial sleeve 10 is rotated to return to its initial position, e.g. to display a dose of zero units.

Medicament delivery device 1 may be used for several injection processes until either the insulin container 3 is empty or the expiration date of the medicament in the medicament delivery device 1 (e.g. 28 days after the first use) is reached.

Furthermore, before using medicament delivery device 1 for the first time, it may be necessary to perform a so-called "prime shot" to remove air from insulin container 3 and needle 4, for instance by selecting two units of insulin and depresses the dosage knob 8 while holding medicament delivery device 1 with the needle 5 upwards. For simplicity of presentation, in the following, it will be assumed that the ejected amounts substantially correspond to the injected doses, so that, for instance the amount of medicament ejected from the medicament delivery device 1 is equal to the dose received by the user. Nevertheless, differences (e.g. losses) between the ejected amounts and the injected doses may need to be taken into account.

Figure 2:
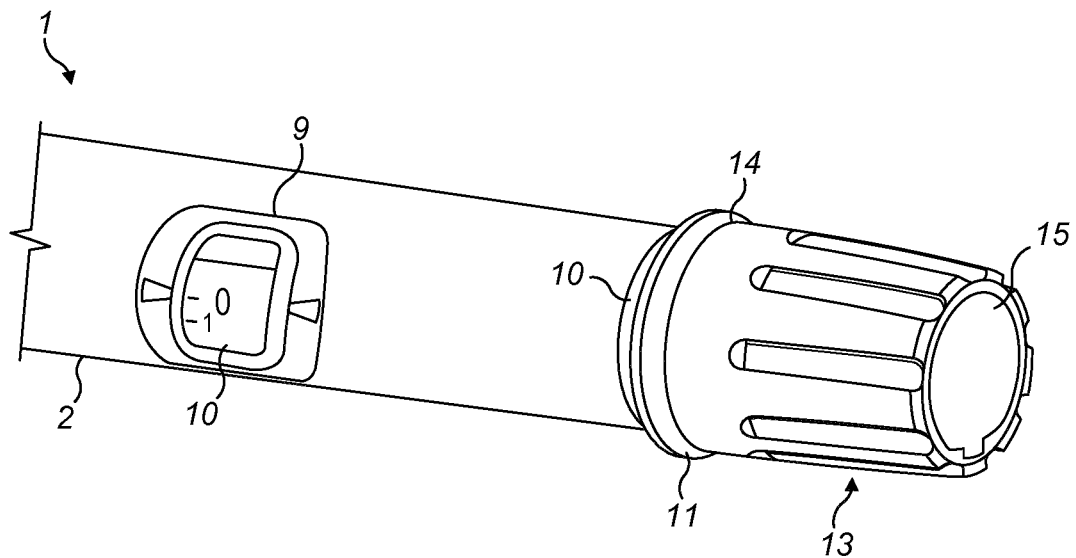
FIG. 2 depicts a data collection device, attached to the injection device of FIG. 1.

FIG. 2 is a perspective view of a data collection device 13 according to an example embodiment attached to one end of the medicament delivery device 1. The data collection device 13 includes a housing 14 with an end plate 15 forming a user interaction surface. The housing 14 may support an optical user feedback such as one or more LEDs (not shown). In some optional embodiments, the data collection device 13 comprises a display (not shown).

The data collection device 13 is compatible with a number of existing medicament delivery devices. The data collection device 13 attaches to the proximal end of the medicament delivery device 1. The data collection device 13 is suitable for attachment to the dose setting dial 12 of the medicament delivery device 1. Attaching a data collection device does not require the dosage knob having formations as shown in FIG. 1. Having a tight fit and/or using rubber-like material at the contact surface between the data collection device and the medicament delivery device would provide an attachment that, on the one hand, facilitates a stable connection in the sense that the two devices remain attached to each other and, on the other hand, allows the two devices to be separated when intended to. The rubber-like material would ensure a proper fit even on a smooth surface, e.g. a dosage knob having a smooth surface such that that rotation of the data collection device causes rotation of the dosage knob and vice versa. The data collection device 13 is compatible with medicament delivery devices where the dose setting dial 1 does not rotate during dose administration, but where the dial sleeve and protrusion(s) 11 do rotate during dose administration. The data collection device 13 is configured to interface with the protrusion(s) such that movement of the protrusion(s) 11 (and thus the dial sleeve) can be detected and measured as the dial sleeve rotates. The data collection device at least partially covers the dose setting dial 12 of the medicament delivery device 1.

Figure 3:
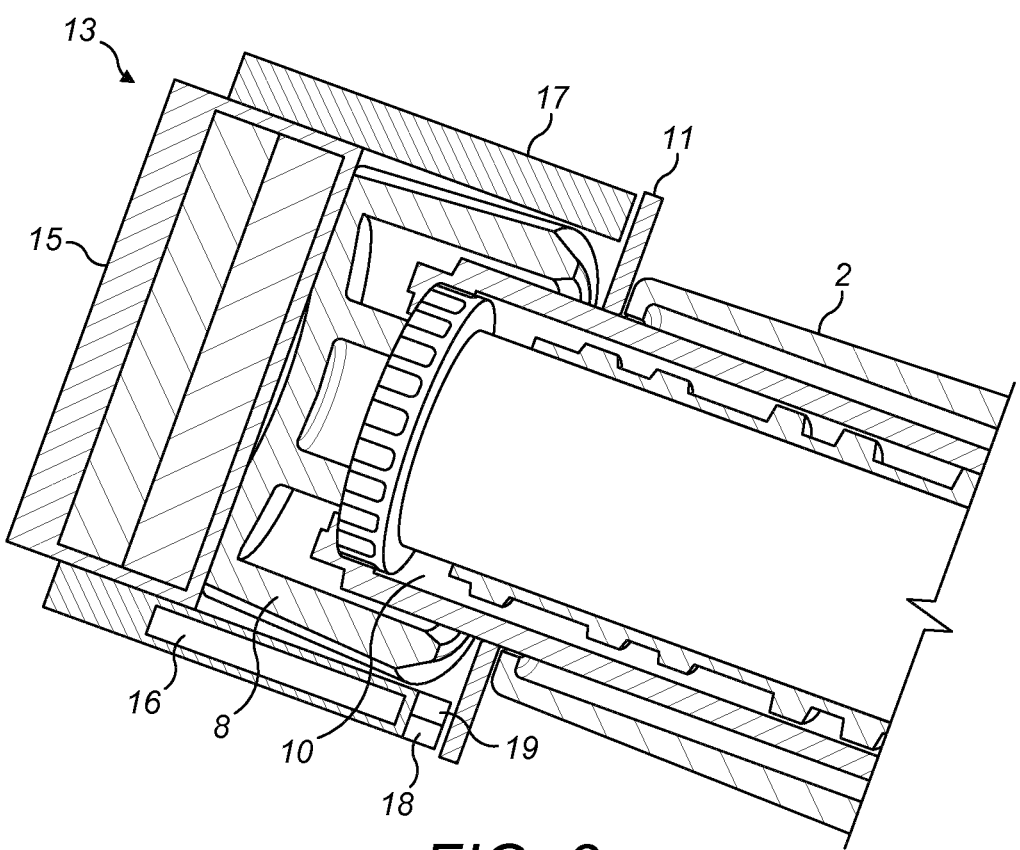
FIGS. 3 and 3a show cross-sectional views of a data collection when attached to the injection device.

FIG. 3 is a cross-sectional view of the data collection device 13 according to some embodiments, attached to a medicament delivery device.

In these embodiments, the medicament delivery device 1 is of a type having a dose setting dial 8 and a clutch (not shown). The dose setting dial 8 is configured to be rotated to set a dose. As the dose setting dial 8 is rotated to set a dose, the dose setting dial 8, dial sleeve 10 and protrusion(s) 11 are engaged by the clutch. Thus, during dose setting, rotation of the dose setting dial 8 also causes dial sleeve 10 and protrusion(s) 11 to rotate. During dose setting, as the dial sleeve 10 rotates it moves out of the housing 12 in a proximal direction away from a proximal edge of the housing 2. During dose setting the dose setting dial also moves in a proximal direction away from the proximal edge of the housing 7.

When a dose is dispensed from the medicament delivery device 1, the dose setting dial 8 is disengaged from the dial sleeve 10 by the clutch. The dose setting dial moves back (distally) towards the proximal end of the housing 2, but does not rotate. The dial sleeve 10 and protrusion 11 rotate during dose dispense and the dial sleeve moves in a distal direction into the housing 12.

When attached to the medicament delivery device 1, the data collection device 13 is configured so as to detect and measure the rotation of the protrusion(s) 11, and thus the rotation of the dial sleeve 10. For example, by detecting the rotation of the protrusion(s) 11, it is possible to measure the angle of rotation (and optionally the number of revolutions) performed by the dial sleeve 10 during dose setting and/or dose dispensing.

The data collection device 13 can have an end plate 15 which has a circular shape and is disposed at a proximal end of the data collection device 13. Extending in a distal direction from the periphery of the end plate 15 are walls that define an attachment assembly 17. The distal end of the data collection device 13 is defined by the edges of the walls. The end plate 15 and walls together define a hollow cavity which is suitable for receiving the dose setting dial 8. Thus, the data collection device has a generally cylindrical shape and has a closed end, defined by plate 15, and an open end which has a generally circular shape and is defined by the distal ends of the walls. When the dose setting dial 8 is received into the hollow cavity of the data collection device 13, the proximal end of the dose setting dial 8 abuts the underside of the end plate 15, whilst the walls of the data collection device envelope the dose setting dial 8 and at least partially cover the formations 12a, 12b and 12c (where present). In some embodiments, the walls of the data collection device 13 may be flared such that the diameter of the end plate 15 is smaller than the diameter of the open end of the data collection device 13. For example, as the walls extend from the end plate 15 they may flare outwards. In such embodiments, the data collection device 13 will have a frustoconical shape.

The data collection device 13 includes a housing 14 and an electronics assembly 16 disposed inside the housing 14. The housing 14 comprises an attachment assembly 17 configured to secure the data collection device 13 to the dose setting dial 8. The dose setting dial 8 may comprise formations (not shown) that can be used to facilitate attachment of the data collection device 13.

In some embodiments, the attachment assembly 17 is a sleeve that is positioned over the dose setting dial 8 through formations (not shown) that co-operate with the formations on the dose setting dial 8 so that, when the dose setting dial 8 rotates during programming of the dosage, the data collection device 13 also rotates. Alternatively, or additionally, resilient padding, such as a foam rubber pad, may be provided within the formations on the attachment assembly 17, to allow for tolerances in the dimensions of the formations on the attachment assembly 17 and the formations on the dose setting dial 8 and/or to provide an engagement between the attachment assembly 17 and the dose setting dial 8 so that rotation of the attachment assembly 17 causes rotation of the dose setting dial 8 and vice versa. Further alternatively, the attachment assembly 17 comprises a resilient padding of sufficient thickness to render formations that co-operate with the formations on the dose setting dial. The padding is soft enough to conform to the surface of the dose setting dial 8. For example, the padding is soft enough to conform to the formations on the surface of the dose setting dial 8.

The electronics assembly 16 is retained within the housing 14. The electronics assembly 14 may comprise a PCB and a battery, for example in the form of a coin cell. The PCB may support a number of components including a processor arrangement, a light source 18 and an optical sensor 19. In these embodiments, the light source 18 is an infrared light source and the optical sensor 19 is an infrared optical sensor.

The light source 18 is arranged within the data collection device 13 and is configured to project light in a direction away from the data collection device and towards a component that is visible outside the device. That is to say, the light source is configured to project light onto an external surface of a component of the medicament delivery device 1. In the present embodiment, the light source 18 is positioned within the attachment assembly 17 and projects light from the distal edge of the attachment assembly 17 towards the distal end of the medicament delivery device 1.

The light source 18 is arranged to illuminate an external surface of a component of the medicament administration device. In the present embodiment, the light source 18 is arranged to project light towards the upper surface of the protrusion(s) 11 of the dial sleeve 10. In such embodiments, when light projected by the light source 18 strikes the upper surface of the protrusion(s) 11, at least a portion of the projected light is reflected from the upper surface. The amount of light reflected from the surface will depend, at least in part, on the relative reflectance of the upper surface. For example, at least part of the upper surface can have characteristics, such as a reflective coating or colour, that causes light projected by the light source to be reflected.

In some embodiments, at least a portion of the upper surface of the protrusion(s) is relatively reflective and is configured to reflect at least some of the light that is projected by the light source 18. The optical sensor 19 is arranged to detect projected light that is reflected from the upper surface of the protrusion(s) 11 of the dial sleeve 10.

In order to allow for projected light to be reflected from the upper surface of the protrusion(s) 11 and then received by the optical sensor 19, there is a gap between the light source 18 (and optical sensor 19) and the upper surface of the protrusion(s) 11.

The protrusion(s) 11 extends from the external surface of the dial sleeve 10 and extends beyond the external surface of the housing 2 and the external surface of the dose setting dial 8. Alternatively, in some embodiments, the protrusion(s) may be flush with the external surface of the housing 2. The protrusion(s) 11 is positioned between the proximal edge of the housing 2 and the distal edge of the dose setting dial 8. As the dial sleeve 10 rotates, the protrusion(s) 11 also rotates. At least a portion of the protrusion(s) 11 is visible externally from the device during ordinary use of the device (i.e. when dialing a dose and dispensing a dose). In other words, the protrusion(s) is not an internal component of the device that cannot be seen during ordinary use (e.g. dose setting and dose dispensing) of the device.

The dial sleeve 10 is a hollow cylinder which is partially located within the housing 12 of the medicament delivery device 1. The dial sleeve extends beyond the proximal end of the housing 12 and is releasably fixed to the dose setting dial 8 by a clutch (not shown). The annular end surface of the dial sleeve 10 therefore sits underneath the dose delivery button 8. The dial sleeve 10 is provided with at least one outward radial protrusion 11 which extends beyond the external surface of the housing 12. The outward radial protrusion 11 allows the data collection device 13 to interface with, and monitor a property of, the medicament delivery device 1.

Figure 3A:
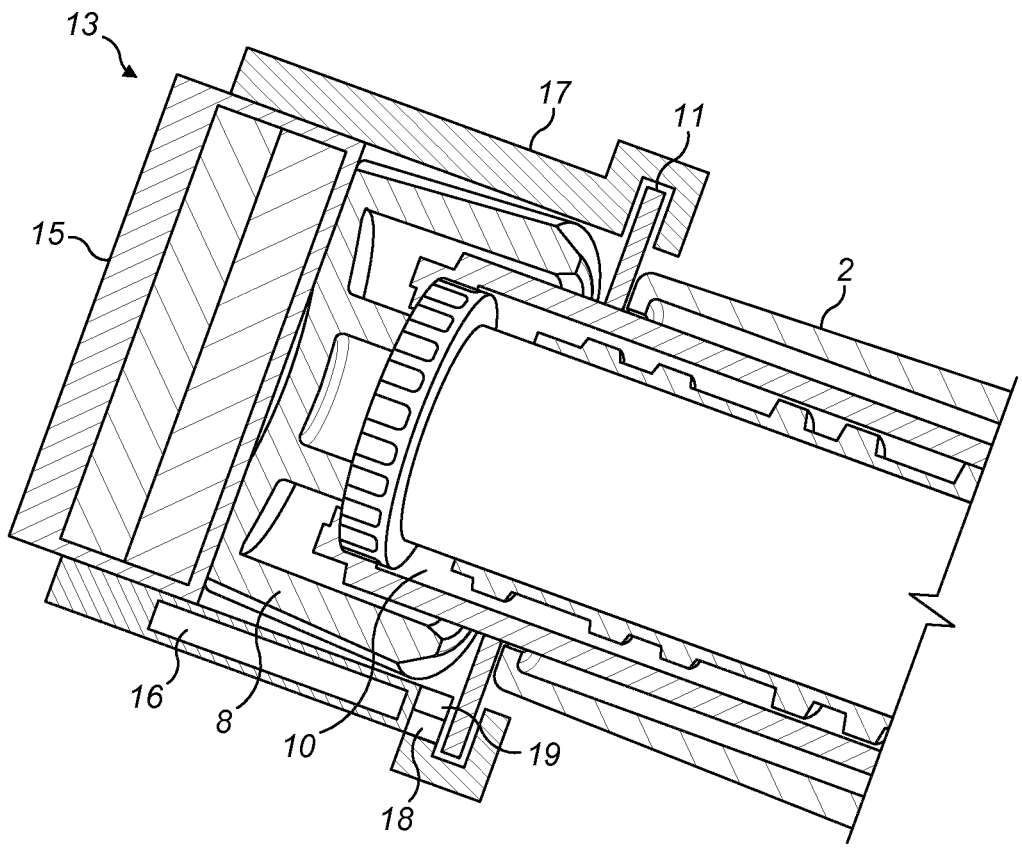

As shown in FIG. 3a, in one alternative embodiment, the protrusion(s) 11 are at least partially enclosed by the walls of the data collection device 13. For example, the walls of the data collection device 13 may extend around the protrusion(s) 11. The extended walls may help protect both the device itself and the protrusion(s) 11 from damage and also provide additional protection against the ingress of foreign matter, such as dust, into the device. In some embodiments, the walls of the data collection device 13 may be deformable or flexible. For example, the walls may be made form a material that has resiliently deformable properties. In such embodiments, the walls of the data collection device may be configured to deform so that the proximal ends of the walls can fit over and partially enclose the protrusion(s). Alternatively, the walls of the data collection device 12 may comprise a hinged component, such as a biased hinge, to enable the walls of the data collection device to be hinged into an open position to receive the protrusion(s) into the data collection device and then biased into a closed position to partially enclose the protrusion(s). This may facilitate mounting of the data collection device 13 onto the medicament delivery device 1 such that the protrusion(s) are at least partially enclosed by the walls of the data collection device 13.

Figure 4A:
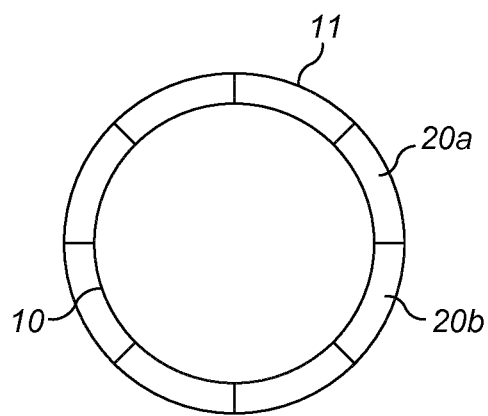
FIGS. 4a and 4b depict a cross-sectional view of the injection device illustrated in FIG. 1.

FIG. 4a is a cross-sectional view of the dial sleeve 10 according to certain embodiments. The dial sleeve 10 comprises a single radial protrusion 11 which extends outwardly beyond the external surface of the housing 12. The protrusion 11 can be in the form of an annular flange having an upper surface and a lower surface. In the illustrated embodiment, the upper surface can be sub-divided into segments 20a and 20b, each segment having a different property, such as a different reflectance. For example, at least a portion of segment 20a can be more reflective compared with the reflectance of segment 20b. The relative reflectance of consecutive segments can vary. For example, equally spaced reflective and non-reflective sections may be arranged alternately.

Figure 4B:
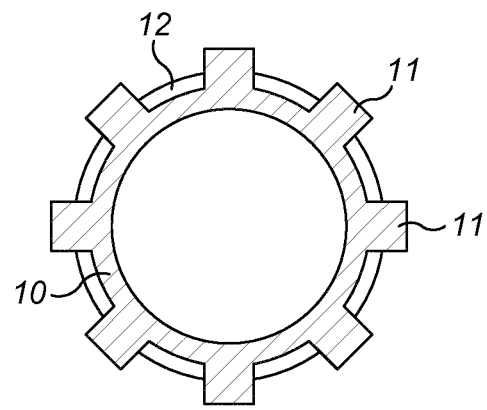

FIG. 4b is a cross-section view of the dial sleeve 10 according to some embodiments. The dial sleeve 10 comprises a plurality of radial protrusions 11 which extend outwardly beyond the external surface of the housing 12. Each of the protrusions 11 has an upper and lower surface. In the illustrated embodiment, each protrusion 11 can have a different property, such as a different reflectance. At least a portion of the upper surface of one or more of the protrusions 11 has properties that allow it to reflect light. For example, at least a portion one protrusion 11 can be more reflective compared with the reflectance of the surface of another protrusion 11. The relative reflectance of protrusions can vary. For example, equally spaced and, and optionally equally sized, reflective and non-reflective protrusions may be arranged alternately. In the illustrated embodiment, the protrusions are equally spaced. However, it will be appreciated that the spacing between adjacent protrusions can vary.

In alternative embodiments, instead of having a light source 18 and optical sensor 19, the electronics assembly may comprise other means for detecting the rotation of the protrusion(s) 11. For example, the light source 18 and optical sensor 19 may be replaced with other non-contact means for detecting the rotation of the protrusion(s) 11, such as magnetic sensors and induction apparatus. Alternatively, the light source 18 and optical sensor 19 may be replaced with contact means for detecting the rotation of the protrusion(s) 11, such as one or more switches which directly contact the protrusion(s) 11 as they turn, e.g. one or more electric contacts configured to contact conductive portions of material disposed on the surface of the protrusion(s) (for example, in place of the relatively reflective regions). Such conductive portions may take the form of conductive tracks, which comprise alternating regions of electrically conductive and electrically insulating material on the surface of the protrusion(s).

In some other alternative embodiments, the electronics assembly comprises a Hall Effect sensor, which is a type of non-contact sensor. In such embodiments, the protrusion(s) 11 of dial sleeve 10 can be at least partially magnetic or have regions that are magnetic. The magnetic regions may be permanent magnets. For example, the protrusions may be at least partially coated with a magnetic material, such as a paint or ink that contains magnetic particles. As the magnetic and non-magnetic regions move past the magnetic sensor during dose dialing and dose dispensing, the magnetic sensor detects a periodic change in the strength and optionally direction of the magnetic field. This information can then be used to determine the amount (angle) of rotation of the dial sleeve 10.

The dose setting dial 8 is configured to be rotated to set a dose. This causes the dial sleeve 10 to also rotate and move in a proximal direction out of the housing 12. When a dose is dispensed from the medicament delivery device 1, the dial sleeve 10 rotates and moves back (distally) inside the housing 12, but the dose setting dial 8 does not rotate. The data collection device 13 is configured so as to detect and measure the rotation of the protrusion(s) 11 when attached to the medicament delivery device 1.

Figure 5:
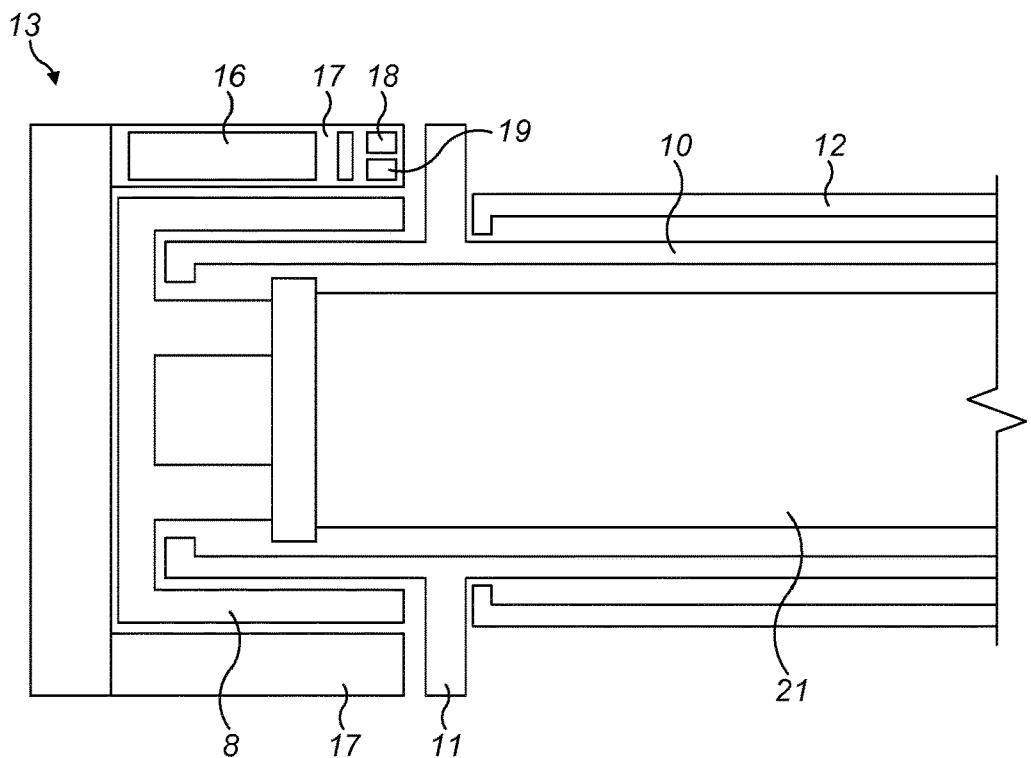
FIGS. 5 and 5a show cross-sectional views of a data collection when attached to the injection device.

The medicament delivery device 1 shown in FIG. 5 may also have other components which rotate when a dose is dispensed, such as a drive sleeve 21.

During a dose dispensing operation, the light source 18 illuminates the upper surface of the protrusion(s) 11 of the dial sleeve 10 including the relatively reflective and non-reflecting regions; and the optical sensor 19 receives the light reflected by at least the relatively reflective regions. During dispensing, the distance (light path) between the light source 18 and optical sensor 19 is shorter than during dialing. The output of the optical sensor 19 is relayed to the processor which calculates an amount of rotation of the protrusion(s) 11, and thus the amount of rotation of the dial sleeve 10, during the dose dispensing operation. From the amount of rotation, the delivered dose can be calculated. This may be done by the data collection device 13 or by another computing device.

FIG. 5 shows a cross-sectional view of the data collection device 13 according to some embodiments, when attached to the medicament delivery device 1 of FIG. 1. The data collection device 13 comprises an attachment assembly 17 and an electronics assembly 16, which may be integral or otherwise fixedly secured together. For example, the attachment assembly 17 may form part of a housing 14 of the data collection device 13, and the housing 14 may also retain the electronics assembly 16.

The attachment assembly 17 is configured to secure the data collection device 13 to the dose setting dial 8. As previously described, the data collection device 13 may employ a simple friction fit to releasably secure it to the dose setting dial 8 and the formations 12a, 12b, 12c on the dose setting dial 8 may be used to facilitate attachment or angular alignment.

When the data collection device 13 and medicament delivery device 1 are secured together, the data collection device 13 effectively replaces the dose setting dial 8, as the user interacts directly with the data collection device 13 in the same way as they would with the dose setting dial to set and deliver a dose of medicament.

The electronics assembly 16 comprises numerous components including a PCB (not shown), the light source 18, the optical sensor 19, a processor arrangement (not shown) and a battery (not shown).

In these embodiments, the light source 18 is an Infrared light source and the optical sensor 9 is an Infrared optical sensor. The dial sleeve may be releasably fixed to the dose setting dial 8 such that the annular end surface of the dial sleeve 10 sits underneath of the proximal end of the dose setting dial 8.

In general it is necessary to know the type of the medicament delivery device 1 to which the data collection device 13 is attached in order to determine a dose of medicament which has been dispensed. Therefore, in some embodiments, the data collection device 13 measures only the amount of rotation of the protrusion(s) 11 in degrees. This information is saved in a memory of the data collection device 13 and may be communicated by the data collection device 13 to an external computing device where it is combined with information about the type of medicament delivery device 1 in order to record the delivered medicament dose.

The fixed construction and design of the embodiment of the data collection device 13 in FIG. 5 has the advantage of a simple mechanical construction (e.g. by minimizing relative movements) which provides an accurately defined positioning of optical sensor 18 relative to the medicament delivery device housing and the protrusion(s) 11 which carry the relatively reflective and non-reflecting regions.

Many previous data collection devices function by illuminating an internal component of a medicament administration device. Such devices may comprise a light source that shines light onto an internal component of the device which comprises a pattern of relatively reflective and non-reflective regions, i.e. such devices do not comprise a component that extends beyond the external surface of the housing of the device and which is visible from the outside of the device. It is difficult to clean the relatively reflective regions of these devices as they are located internally within the device and are thus relatively difficult to access.

Moreover, where the dial sleeve comprises more than one protrusion 11, the gap formed between adjacent protrusions 11 provides clearly defines the separation between adjacent protrusions 11, thereby further improving the reliability of the device and reducing the incidence of false signals and the like.

The data collection device of the present disclosure attaches directly to the dose setting 8 dial of the medicament administration device. Previous data collection devices have attached to the main housing of the medicament administration device. This can impede the use of the medicament administration device by a user. Many such devices attach over a dose indication window in the housing of the medicament administration device. This obscures the dose indication window, making the user wholly reliant on the data collection device to indicate the dialed dose, which may reduce user confidence in the medicament administration device.

Some other such devices require an additional cut out or aperture in the housing of the medicament administration device in order to view or connect with an internal moveable component. Cutting out a part in the housing of the medicament administration device makes the ingress of dust and dirt inside the delivery mechanism more likely. It may also present problems relating to the sterility of the medicament administration device.

The data collection device of the present disclosure is able to monitor the amount of medicament dispensed from the medicament administration device remotely, without contacting or being secured to the main housing of the medicament administration device. The data collection device is configured to attach to and to effectively replace the part of the medicament administration device with which the user would normally interact. When a user wishes to dial a dose, they grasp and rotate the housing 21 of the data collection device 20 which in turn rotates the dose setting dial 12. The user can continue to observe the mechanical dose indication window 13 of the medicament administration device. When the user wishes to inject a dose, they exert a force on the proximal end of the data collection device. This in turn communicates a force to the dose setting dial.

The data collection device of the present disclosure may use infrared light as an illumination source.

Where the dial sleeve comprises a single protrusion 11 (for example, a flange) which extends circumferentially around the dial sleeve, the relatively reflective and non-reflective regions may be printed, deposited, etched or otherwise created directly onto the upper surface of the protrusion 11 of the dial sleeve 10. Despite the addition of the at least one protrusion 11, the medicament administration device may then be assembled in the same way as before, using the same assembly method and tools. Therefore, only very minimal modification of the medicament administration device design and creation is required in order to implement the invention.

As discussed above, the light source 18 and optical sensor 19 may instead be replaced with a magnetic sensor. Where the dial sleeve comprises a single protrusion (for example, a flange) the relatively reflective and non-reflective sections 20a and 20b of the protrusion may be replaced by alternating magnetic regions and non-magnetic regions such that when the dial sleeve 10 and thus the protrusion 11 is rotated during a dose dispensing operation, there is a periodic change in the magnetic field detected by the magnetic sensor.

Figure 5A:
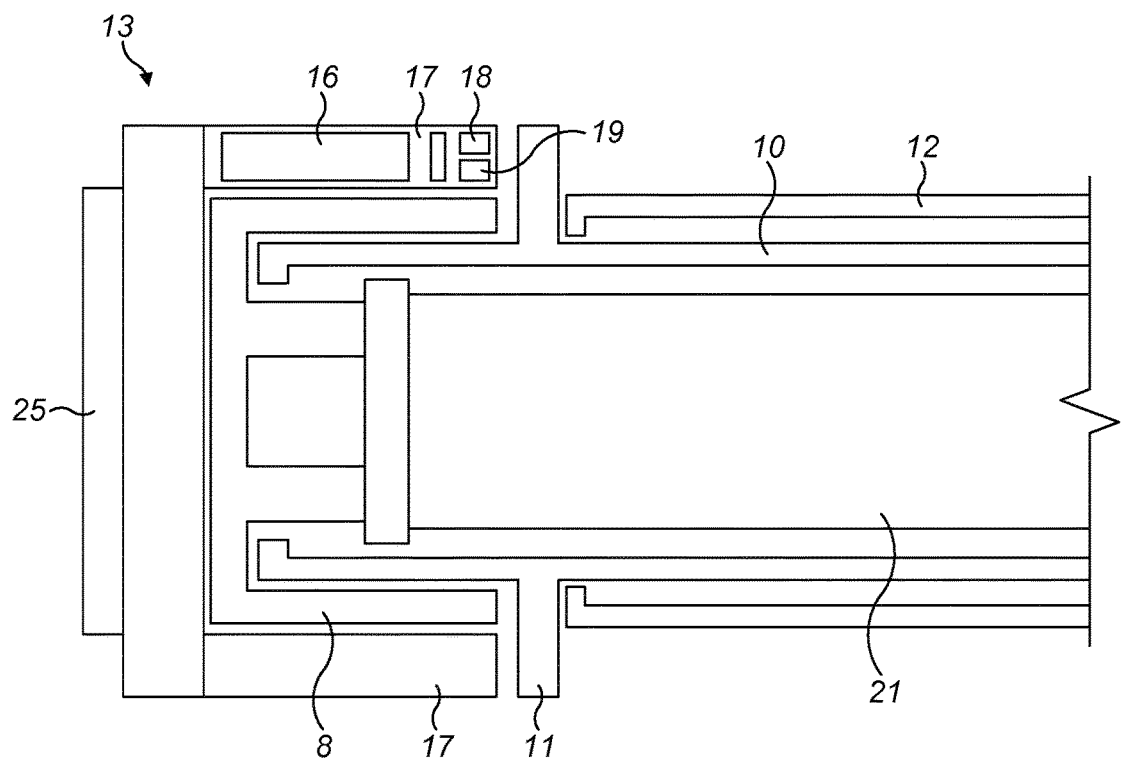

FIG. 5a shows a cross-sectional view of the data collection device 13 according to an alternative embodiment, when attached to the medicament delivery device 1 of FIG. 1. In such embodiments, the data collection device comprises a switch 25 which is in association with, or forms an integral part of, the electronics assembly 16. The switch 25 may be used to operate the device, i.e. to turn the device on and off. The switch may also perform a number of other functions and therefore be described as a multi-function button. For example, the switch may be depressed to prompt the data collection device to begin measuring the rotation of the protrusion(s) and start measuring the dose of medicament. In the embodiment illustrated, the switch is a component that is visible externally from the data collection device and can be depressed by the user of the device, for example by the user's thumb pressing the switch. Alternatively, the switch may be an internal component of the data collection device that is triggered by other means, such as movement of the protrusions relative to the device, rather than by the user directly operating it.

Figure 6:
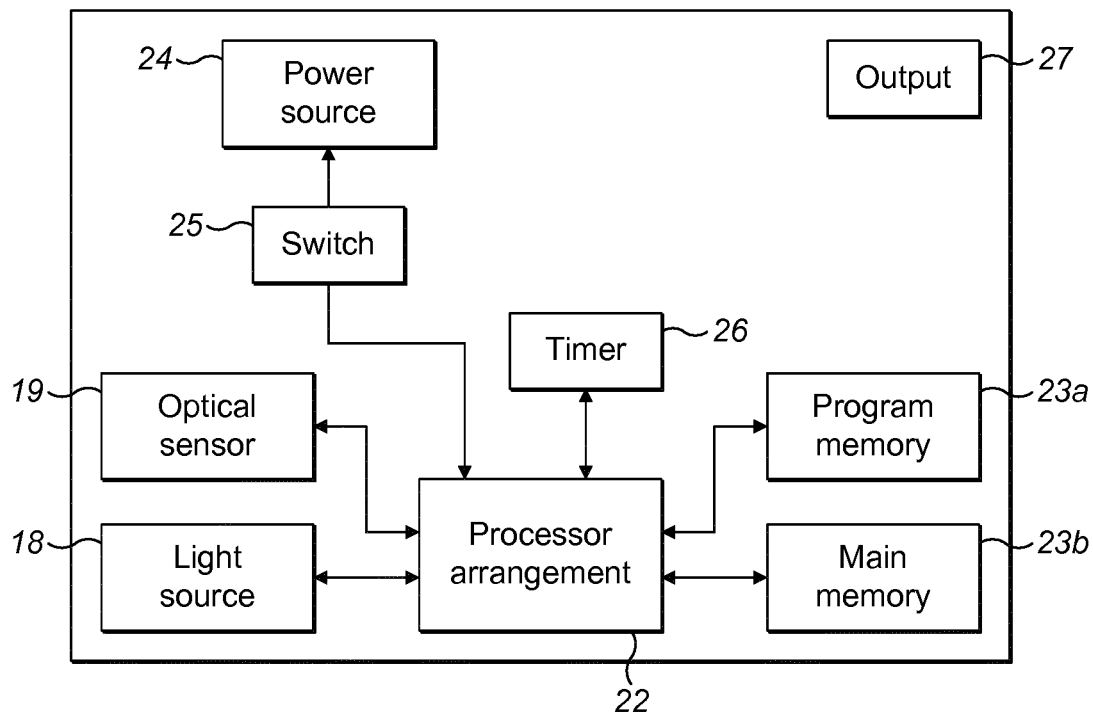
FIG. 6 is a block diagram of the data collection device.

FIG. 6 is a block diagram of the data collection device 13. The data collection device 13 includes a processor arrangement 22 including one or more processors, such as a microprocessor, a Digital Signal Processor (DSP), Application Specific Integrated Circuit (ASIC), Field Programmable Gate Array (FPGA) or the like, together with memory units 23a, 23b, including program memory 23a and main memory 23b, which can store software for execution by the processor arrangement 22. The data collection device includes the Infrared light source 18 and the Infrared optical sensor 19. The processor arrangement 22 controls operation of the light source 18 and the optical sensor 19 and receives signals from the optical sensor 19.

The data collection device 13 has a power source 24 which may be a battery, for example a coin cell. As mentioned previously, the data collection device 13 may optionally include a switch 25 configured to be triggered when or shortly before a dose is dispensed. For example, the switch may act as a "wake-up" switch and prompt the device to go from an inactive (i.e. powered-down) state to an active (i.e. powered-up) state. To this end, the switch 25 may include a pressure or touch sensitive area in the end plate 15 of the data collection device 13, for example a piezoelectric switch. The switch 25 may control application of power from the power source 24 to the processor arrangement 22 and other components of the data collection device 13. In embodiments in which the electronics assembly 16 and attachment assembly 17 are configured to move longitudinally relative to each other, the switch 25 may be implemented mechanically.

The wake-up switch may be implemented in a number of ways. For example, the wake-up switch may be implemented optically as an "optical wake-up sensor", inductively as an "inductive wake-up sensor" or using capacitive sensing, e.g. using a "capacity wake-up sensor". Where an optical wake-up sensor is employed, the dose setting dial 8 of the medicament delivery device 1 may be colored, for example green, while a portion of the upper surface of the protrusion(s) 11 may be white (or black). During dose delivery, the protrusion(s) 11 moves in front of the optical wake-up sensor and the change in reflectance and/or color can be detected, providing the wake-up signal for the other electronics. This change in reflectance or color can also be used to determine the start and end times of an injection process. In this case a switch as described before may function to wake-up the electronics, including the light source and optical sensor and an optical switch may use the change in reflectance or color to determine start and end times of an injection process. This could be helpful in determining if an injection process has occurred or if a priming process has occurred. Further, the color/reflectance switch could be used to determine how long the button has been pressed and use this to see if a dwell time has been respected by the user.

A timer 26 is also included. The processor arrangement 22 may use the timer 26 to monitor a length of time that has elapsed since an injection was completed, determined using the switch 25. Also optionally, the processor arrangement 22 may compare the elapsed time with a predetermined threshold, to determine whether a user may be attempting to administer another injection too soon after a previous injection and, if so, generate an alert such as an audible signal and/or generate an optical signal such as blinking one or more LEDs. The data collection device 13 may comprise a number of LEDs or other light sources for providing optical feedback to a user. For example, the LEDs may use different colors and/or lighting patterns such as blinking with constant or changing periodicity. On the other hand, if the elapsed time is very short, it may indicate that the user is administering a medicament amount as a "split dose", and the processor arrangement 22 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor arrangement 22 stores information indicating that the dosage was delivered as a "split dose". Another optional purpose for monitoring the elapsed time by the processor arrangement 22 is to determine when the elapsed time has passed a predetermined threshold, suggesting that the user might have forgotten to administer another injection and, if so, generate an alert.

The processor is further configured to store data relating to date and/or time information, data relating to information from the optical sensor 19, or combinations thereof. In particular, the memory is configured to store a combination of date and/or time information and internal component rotation information retrieved from the optical sensor 19 output data. In this way the memory is able to store a log that provides a history of information on dial sleeve 10 (or other internal component) rotation. Data can for example be stored in the main memory 23b. Alternatively, data may be stored is a separate data storage section (not shown) of the memory.

Since the dial sleeve rotates as medicament is expelled from the medicament delivery device 1, the angle of rotation measured by the optical sensor 19 is proportional to the amount of medicament expelled. It is not necessary to determine a zero level or an absolute amount of medicament contained in the medicament delivery device 1. In this way the sensor arrangement is less complex than compared to a sensor arrangement that is configured for absolute position detection. Moreover, since it is not necessary to monitor the numbers or tick marks on the dial sleeve 10 displayed through the dosage window 9, the data collection device 13 may be designed so that it does not obscure the dosage window 9.

Figure 7:
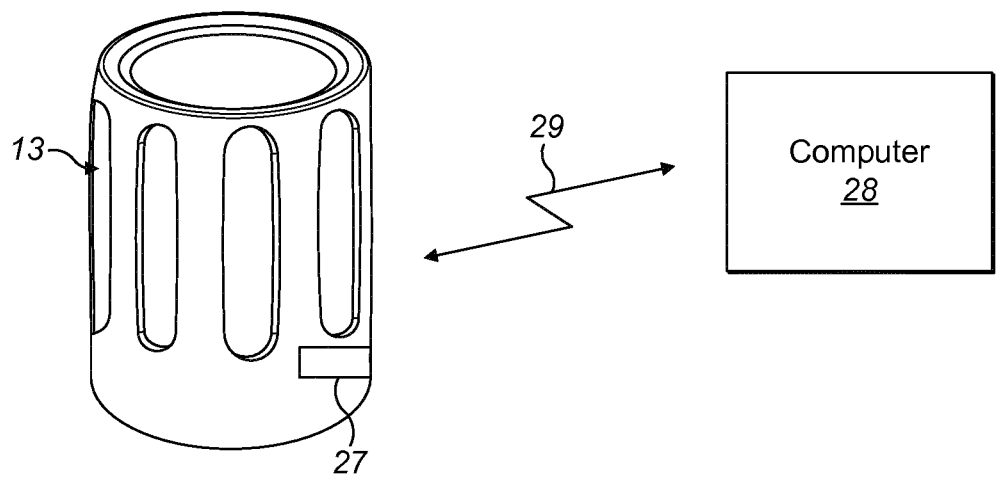
FIG. 7 shows a system in which the data collection device is connected to another device, such as a personal computer.

An output 27 is provided, which may be a wireless communications interface for communicating with another device via a wireless network such as wi-fi, Bluetooth®, or NFC, or an interface for a wired communications link, such as a socket for receiving a Universal Series Bus (USB), mini-USB or micro-USB connector. FIG. 7 depicts an example of a system in which the data collection device 13 is connected to another device, such as a personal computer 28, via a wireless connection 29 for data transfer. Alternatively or in addition, the data collection device 13 may be connected to another device via a wired connection. For example, the processor arrangement 16 may store determined dial sleeve 10 rotation angles and time stamps (including date and/or time) for the injections as they are administered by the user and subsequently, transfer that stored data to the computer 28. The computer 28 may be configured to calculate an administered dose based on further information entered by the user or a medical professional regarding the type of medicament delivery device and the type of medicament. The computer 28 maintains a treatment log and/or forwards treatment history information to a remote location, for instance, for review by a medical professional.

According to some embodiments, the data collection device 13 may be configured to store data such as dial sleeve 10 rotation angles and time stamps of up to 35 injection events. According to a once-daily injection therapy this would be sufficient to store a treatment history of about one month. Data storage is organized in a first-in first-out manner ensuring that most recent injection events are always present in the memory of the data collection device 13. Once transferred to a computer 28 the injection event history in the data collection device 13 will be deleted. Alternatively, the data remains in the data collection device 13 and the oldest data is deleted automatically once new data is stored. This way the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the output 27 may be configured to transmit information using a wireless communications link and/or the processor arrangement 13 may be configured to transmit such information to the computer 60 periodically.

The specific embodiments described in detail above are intended merely as examples of how the present invention may be implemented. Many variations in the configuration of the data collection device 13 and/or the medicament delivery device 1 may be conceived.

In particular, while the embodiments above have been described in relation to collecting data from an insulin injector pen, it is noted that embodiments of the disclosure may be used for other purposes, such as monitoring of injections of other medicaments. Although the data collection device has been described primarily as comprising a single Infrared light source 18, the data collection device may comprise a plurality of light sources 18. The plurality of light sources 18 may be supported at different positions on the electronics assembly 16 and/or the attachment assembly 17 as long as they are angled and or focused so as to illuminate a particular part of the protrusion 11 of the dial sleeve 10 from a particular angle when the data collection device is attached to the dose setting dial.

The data collection device 13 may optionally include a display (not shown), which could for example occupy the end plate 15 of the data collection device 13. Various information can be displayed, such as the length of time that has elapsed since an injection was completed, and warning messages where a user is attempting to administer another injection too soon after a previous injection.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis. Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

The invention claimed is:

1. A data collection device comprising:
a distal end, the distal end being open to allow the data collection device to be mounted on a rotatable dose setting dial of a medicament administration device;
a proximal end, the proximal end being closed;
a light source configured to project light from the distal end of the data collection device; and
an optical sensor, wherein when the data collection device is mounted on the dose setting dial of the medicament administration device:
the distal end of the data collection device faces a surface of at least one outward radial protrusion extending beyond an external surface of an external housing of the medicament administration device and the light source is configured to illuminate a portion of the surface of the at least one outward radial protrusion, wherein the at least one outward radial protrusion is located distally with respect to the data collection device and is part of a dial sleeve of the medicament administration device located partially inside the external housing of the medicament administration device and configured to rotate when a dose is dialed; and the optical sensor faces the surface of the at least one outward radial protrusion of the dial sleeve and is configured to receive light reflected by at least relatively reflective regions disposed on the surface of the at least one outward radial protrusion of the dial sleeve.

2. The data collection device of claim 1, wherein the data collection device comprises an electronics assembly comprising the light source and the optical sensor.

3. The data collection device of claim 2, wherein the electronics assembly comprises a processor configured to receive signals from the optical sensor and to detect an occurrence of a medicament delivery from the medicament administration device.

4. The data collection device of claim 3, wherein the processor is configured to receive signals from the optical sensor and to determine an amount of rotation of the dial sleeve of the medicament administration device.

5. The data collection device of claim 4, wherein the data collection device is configured to determine a dialed dose.

6. The data collection device of claim 1, wherein the light source is an infrared light source.

7. A medicament administration device comprising:
a housing having a proximal end and a distal end;
a rotatable dial sleeve located partially inside the housing, the rotatable dial sleeve having a proximal end and a distal end; and
a dose setting dial coupled via a clutch to the proximal end of the dial sleeve, wherein the dial sleeve comprises at least one outward radial protrusion arranged between the proximal end of the housing and a distal end of the dose setting dial and a relatively reflective portion on a proximal surface of the at least one outward radial protrusion of the dial sleeve, wherein the medicament administration device is configured such that the rotatable dial sleeve and the at least one outward radial protrusion are rotationally coupled with the dose setting dial during dose setting and the rotatable dial sleeve and the at least one outward radial protrusion are rotationally decoupled from, and rotate relative to, the dose setting dial during dose delivery.

8. The medicament administration device of claim 7, wherein the at least one outward radial protrusion of the dial sleeve extends beyond an external surface of the housing.

9. The medicament administration device of claim 7, wherein the at least one outward radial protrusion of the dial sleeve comprises a plurality of teeth.

10. The medicament administration device of claim 9, wherein the teeth comprise relatively reflective portions formed on a surface of the teeth.

11. The medicament administration device of claim 7, wherein the at least one outward radial protrusion of the dial sleeve is an annular flange.

12. A system comprising:
a medicament administration device comprising a housing having a proximal end and a distal end;
a rotatable dial sleeve located partially inside the housing, the rotatable dial sleeve having a proximal end and a distal end;
a dose setting dial coupled via a clutch to the proximal end of the dial sleeve, wherein the dial sleeve comprises at least one outward radial protrusion arranged between the proximal end of the housing and the dose setting dial and extending beyond an external surface of an external housing of the medicament administration device; and
a data collection device configured to be mounted on the dose setting dial of the medicament administration device, the data collection device comprising:
a light source; and
an optical sensor, wherein the light source is configured to illuminate a portion of a surface of the at least one outward radial protrusion of the dial sleeve, and wherein the optical sensor is configured to receive light reflected by at least relatively reflective regions disposed on the surface of the at least one outward radial protrusion of the dial sleeve and incident on the distal end of the data collection device.

13. The system of claim 12, wherein the data collection device is mounted on the dose setting dial of the medicament administration device.

14. The system of claim 12, wherein when the data collection device is mounted on the dose setting dial, a distal end of the data collection device faces the at least one outward radial protrusion of the dial sleeve of the medicament administration device.

15. The system of claim 12, wherein:
the data collection device comprises an electronics assembly comprising the light source and the optical sensor,
the electronics assembly comprises a processor configured to receive signals from the optical sensor and to detect an occurrence of a medicament delivery from the medicament administration device, and
the processor is configured to receive signals from the optical sensor and to determine an amount of rotation of the dial sleeve of the medicament administration device, and the data collection device is configured to determine a dialed dose.

16. The system of claim 12, wherein the light source is an infrared light source.

* * * * *